US012600786B2

(12) United States Patent  
Papasotiriou

(10) Patent No.: US 12,600,786 B2  
(45) Date of Patent: Apr. 14, 2026

(54) C-MET AND TMX2 ANTIBODIES

(71) Applicant: R.G.C.C. Holdings AG, Zug (CH)

(72) Inventor: Ioannis Papasotiriou, Oberägeri (CH)

(73) Assignee: R.G.C.C. Holdings AG, Zug (CH)

( * ) Notice: Subject to any disclaimer, the term of this patent is extended or adjusted under 35 U.S.C. 154(b) by 1321 days.

(21) Appl. No.: 17/292,907

(22) PCT Filed: Nov. 18, 2019

(86) PCT No.: PCT/EP2019/081597  
§ 371 (c)(1),  
(2) Date: May 11, 2021

(87) PCT Pub. No.: WO2020/099674  
PCT Pub. Date: May 22, 2020

(65) Prior Publication Data  
US 2022/0002421 A1     Jan. 6, 2022

(30) Foreign Application Priority Data  
Nov. 16, 2018   (EP) ..................................... 18206795

(51) Int. Cl.  
*C12N 5/0784*     (2010.01)  
*C07K 16/28*     (2006.01)  
*C12N 5/0781*     (2010.01)  
*G01N 33/68*     (2006.01)

(52) U.S. Cl.  
CPC ........ *C07K 16/2863* (2013.01); *C12N 5/0635* (2013.01); *C12N 5/0639* (2013.01); *G01N 33/6854* (2013.01); *C07K 2317/14* (2013.01); *C07K 2317/21* (2013.01); *C12N 2501/22* (2013.01); *C12N 2501/2304* (2013.01); *C12N 2501/2306* (2013.01); *C12N 2501/231* (2013.01); *C12N 2501/2321* (2013.01); *C12N 2501/25* (2013.01); *G01N 2333/71* (2013.01)

(58) Field of Classification Search  
CPC ........... C07K 16/2863; C07K 2317/14; C07K 2317/21; C07K 2317/34; C07K 2317/73; C07K 16/28; C07K 16/30; C07K 16/40; C07K 16/00; C12N 5/0635; C12N 5/0639; C12N 2501/22; C12N 2501/2304; C12N 2501/2306; C12N 2501/231; C12N 2501/2321; C12N 2501/25; C12N 2501/505; C12N 2501/599; C12N 2502/1121; C12N 2506/115; G01N 33/6854; G01N 2333/71  
See application file for complete search history.

(56) References Cited

U.S. PATENT DOCUMENTS

2005/0054019 A1   3/2005   Michaud et al.  
2009/0175860 A1   7/2009   Stover et al.  
2013/0196380 A1   8/2013   Lueke et al.

FOREIGN PATENT DOCUMENTS

EP     2574666 A1 *   4/2013   ............. C07K 16/00  
KR   10-2012-0140097 A   12/2012  
WO   WO-2011023705 A1 *   3/2011   ............. C07K 16/00  
WO   2013/192594 A2   12/2013

OTHER PUBLICATIONS

Knudsen et al., Article or Chapter Title A Novel Multipurpose Monoclonal Antibody for Evaluating Human c-Met Expression in Preclinical and Clinical Settings, in Applied Immunohistochemistry & Molecular Morphology 17(1): 57-67. (Year: 2009).*  
Toloudi M, Papadimitriou M, Pantopikou K, Papasotiriou I. Generation of Human Antibodies Against a Specific Peptide: a Novel Strategy Based on Human Cells. Anticancer Res. Sep. 2016;36(9):4613-21 (Year: 2016).*  
Tomita et al., Hybridoma technologies for antibody production, Immunotherapy, 3(3):371-380 (Year: 2011).*  
Maria Toloudi et al. "Generation of Human Antibodies Against a Specific Peptide: a Novel Strategy Based on Human Cells", Anticancer Research, 2016, vol. 36, pp. 4613-4621 (Year: 2016).*  
Yang AX, Chong N, Jiang Y, Catalano J, Puri RK, Khleif SN. Molecular characterization of antigen-peptide pulsed dendritic cells: immature dendritic cells develop a distinct molecular profile when pulsed with antigen peptide. PLoS One. Jan. 27, 2014;9(1) (Year: 2014).*  
Miltenyi Biotec. B Cell Isolation Kit II. Miltenyi Biotec. 2020. (Year: 2020).*  
Xu Fang, et al., "Rapid de novo generation of antigen specific human B cells with expression of Blimp-1 and AID by in vitro immunization", Experimental Cell Research, Mar. 1, 2017, pp. 53-62, vol. 352, No. 1 (10 pages).  
Neil R. Michaud, et al., "Biochemical and pharmacological characterization of human c-Met neutralizing monoclonal antibody CE-355621", MABS, Nov. 1, 2012, pp. 710-723, vol. 4, No. 6 (14 pages).  
"Naïve B Cell Isolation Kit II", human, MACS, Miltenyi Biotec, Jan. 1, 2017 (2 pages).  
"Datasheet for ABIN6059330 anti-TMX2 antibody (Thioredoxin-Related Transmembrane Protein 2) (AA 49-102)", antibodies-online. com, Oct. 7, 2019, pp. 1-2 (3 pages).  
"Thioredoxin Related Transmembrane Protein 2 (TMX2) Antibody Catalogue No. abx301975", www.abbexa.com, Jan. 1, 2019, p. 1 (1 page).

(Continued)

*Primary Examiner* — Jeffrey Stucker  
(74) *Attorney, Agent, or Firm* — Sughrue Mion, PLLC

(57) ABSTRACT

The present invention provides: a novel method for the production of truly fully human monoclonal antibodies against specific antigens of our choice using isolated human blood cells. These antigens may include but are not limited to peptide sequences found in c-met and TMX2 proteins; an antibody specific for c-met protein produced with said method; an antibody specific for TMX2 protein produced with said method; and a new means and method for the diagnosis, prevention and/or cancer treatment by means of the aforementioned antibodies.

2 Claims, 11 Drawing Sheets

Specification includes a Sequence Listing.

(56) References Cited

OTHER PUBLICATIONS

"Anti-TMX2 Product Datasheet", Atlas Antibodies I Primary Antibodies and Targeted Proteomics—Atlas Antibodies, Dec. 1, 2012, p. 1 (1 page).

"TMX2 Gene-GeneCards", Genecards Human Gene Database, Jan. 1, 2019, pp. 1-15 (15 pages).

Eleana Hatzidaki, et al., "Novel antibody against TMX2 and its effects on breast cancer cells", Int. J. Biochem Mol Biol, Feb. 15, 2020, pp. 1-10, vol. 11, No. 1 (10 pages).

International Search Report for PCT/EP2019/081597 dated May 28, 2020 [PCT/ISA/210] (10 pages).

Written Opinion for PCT/EP2019/081597 dated May 28, 2020 [PCT/ISA/237] (16 pages).

Maria Toloudi et al., "Generation of Human Antibodies Against a Specific Peptide: a Novel Strategy Based on Human Cells", Anticancer Research, 2016, vol. 36, pp. 4613-4621 (9 total pages).

* cited by examiner

| Marker | Left, Right | Events | % Gated | % Total | Mean | CV | Median | Peak Ch |
|--------|-------------|--------|---------|---------|-------|--------|--------|---------|
| All | 1, 9910 | 20000 | 100.00 | 100.00 | 20.00 | 146.21 | 14.72 | 1 |
| M1 | 24, 9910 | 4438 | 22.19 | 22.19 | 47.93 | 108.65 | 33.68 | 25 |

| Marker | Left, Right | Events | % Gated | % Total | Mean | CV | Median | Peak Ch |
|--------|-------------|--------|---------|---------|-------|--------|--------|---------|
| All | 1, 9910 | 20000 | 100.00 | 100.00 | 25.45 | 632.05 | 10.75 | 1 |
| M1 | 24, 9910 | 3803 | 19.02 | 19.02 | 92.53 | 518.42 | 37.18 | 24 | c-met protein detection by western blot using purified supernatants as primary antibody c-met protein detection by western blot using purified supernatants as primary antibody vs commercial antibody The effect of CD138 supernatants on MCF-7 cell viability □ Control  ■ HGF  ▥ Fused supernatants  ▤ HGF+Fused supernatants

C-MET AND TMX2 ANTIBODIES

TECHNICAL FIELD

The present invention relates to techniques in the field of antibodies and their production. More particularly, the present invention relates to a method for producing human monoclonal antibodies that are specific for a specific antigen. This invention also relates to an antibody against c-met and an antibody against TMX2 and the use of these antibodies in diagnosing, preventing and/or treating malignant tumors or any other disease involving an aberrant expression of c-met and/or TMX2.

PRIOR ART

Monoclonal antibody therapies have been approved for over 30 targets and diseases with cancer being at the top. The first generation monoclonal antibodies were of murine origin and as such, unsuitable for therapeutic use due to human anti-mouse antibody response (HAMA). As recombinant DNA technology evolved, a second generation of monoclonal antibodies using chimerization or humanization was developed, thus making the antibodies more human-like. For this, genetic engineering is used to generate antibodies with human constant domains in order to decrease immunogenicity and mouse variable domains for specificity. However, humanization does not entirely and predictably preclude serious side-effect such as catastrophic system organ failures, as has been documented in the case of Theralizumab. It is thus desirable to provide fully human antibodies to avoid such side-effect arising from non-human fragments in the antibody. However, the term "fully human" can be considered misleading since antibodies, which have been designated as "fully human" have in fact a human sequence but they originate from either bacteriophages, transgenic animals or from B cell transformation. It can thus not be warranted that such antibodies are identical, in both structure and immunogenicity, to endogenously produced antibodies. Therefore, in the context of the present invention, the term "fully human antibodies" relates to antibodies that not only have a human sequence but are also produced by human cells, just as in the in vivo process. In particular, the human cells that are employed are autologous cells to further reduce side-effects based on immunogenicity. The previously used techniques do not come without problems; and in the case of B cell transformation, the B cells producing antibodies have to be selected and then immortalized by Epstein-Barr virus (EBV) and while in vitro infection efficiency is generally high, only a small percentage of cells actually become transformed (~1-3%). Inefficiency, instability, low yield and affinity are the characteristics of EBV transformation technology. Phage display technology involves antibody-library preparation first, followed by ligation of the variable heavy and light PCR products into a vector and finally in vitro selection of monoclonal antibody (mAb) clones. However, phage display may not recover all antigen-specific mAbs present in a given antibody library, and in vitro pairing may not reflect the in vivo process and is a complicated, demanding, and time-consuming technology. In transgenic animals, human antibody genes are inserted into for example a mouse genome, enabling human antibody production. However, the human body carries a collection of millions of antibodies and transgenic mice can only express a small fraction of this diversity. Therefore limited germline repertoire, low protein expression, residual immunogenicity and the high cost and labor involved are important drawbacks of DNA recombinant technology. However, the greatest problem of all is the simple fact that they are all essentially hybrids. There is thus a need to provide means that will enable the provision of monoclonal antibodies that can be directed against a given antigen and which are less or not immunogenic in the human body and thus limit undesirable side-effects due to immunogenicity. Of the five antibody classes, IgG is the most frequently used for cancer immunotherapy because it is a potent activator of the immune system.

Previous attempts have been made for the production of human monoclonal antibodies. Fang Xu et al (2017) produced IgM human antibody by activating T cells with pulsed DCs. Then separately activated B cells with the addition of CpG, ODN or KLH and then finally combining the activated T cells with the activated B cells.

However, using CpG, ODN or ssRNA, which are human analogues of DNA microbial motifs, for cell activation and to mount a more pronounced immune response can lead to the production of antibodies against the CpG, ODNs or ssRNAs used along with the antigen of choice. Since they are normal occurring parts of human DNA, where enzymes like methyltransferases bind, the production and binding of such unwanted antibodies to their target could affect normal homeostasis. Moreover, CpG induces T-cell independent differentiation and antibodies generated this way tend to have lower affinity and are less functionally versatile.

WO 2011/023705 concerns the production of human IgG antibodies by activating T-cells with pulsed DCs, and then activating B-cells with activated T-cells. Once more, aActivation is achieved with by the use of CpG, ODN or ssRNA as well as factors like IL-12 and IFN-γ antibodies.

US 2013/0196380 concerns the production of human IgG by activating T-cells with pulsed DCs in the presence of factors like IL-4, IL-5, IL-6 and IL-10. B-cells were separately activated with the used of CpG and then added to activated T-cells.

There are also attempts to produce antibodies ex-vivo using murine cells as stated in EP 2 574 666 A1.

SUMMARY OF THE INVENTION

Accordingly, the present invention has for its object to provide a novel process for the production of a truly fully human monoclonal antibody from isolated human blood cells, which can be directed against a specific antigen of choice, thereby circumventing the above-mentioned problems that may be encountered when producing antibodies from antibody libraries through the techniques such as bacteriophages, transgenic animals or from B cell transformation. In addition, the present invention allows to broaden the range of antigens can be used in the production of a truly fully monoclonal antibodies. The antibodies obtained are not a product of genetic engineering of the cells and are not produced in a transgenic animal.

C-met is a receptor tyrosine kinase that upon binding with its ligand, hepatocyte growth factor (HGF), activates downstream pathways with diverse cellular results. Aberrant c-met signaling has been described in a variety of cancer types, and the receptor is regarded as a novel therapeutic target. C-met activation downstream signaling involves Rac1/Cdc42 pathway, PI3K/Akt pathway, signal transducer and activator of transcription 3 and the ERK/MAPK cascade.

Thioredoxin-related transmembrane protein 2 (TMX2) participates in redox reactions. The reaction oxygen species (ROS) are important for cell signaling and homeostasis, as abnormal regulation is involved in cell proliferation and carcinogenesis among others. Although its function is not fully elucidated, it has been found that TMX2 exhibits high levels of gene expression in breast cancer and specifically in breast CSCs, while the levels are lower in colon and lung cancer. Thereby, TMX2 may be used as a specific biomarker for breast cancer and breast CSCs.

In the process of the present invention, by mimicking natural mechanisms found in the adaptive immune system, dendritic, CD4+ and CD19+ cells are driven towards Th2 immunity where newly formed plasma cells then produce the antibody against the antigen of choice, depending on the antigen used. Cell activation, both dendritic, CD4+ and CD19+, is succeeded by a cytokine cocktail simulating the in vivo inflammatory environment, whereas IgG production can be promoted by IgG class switching factors. The used antigens to obtain the desired antibody are peptides that were chosen for their ability to elicit immune responses. As a result of the process according to the present invention, CD138+ cells, also known as plasma or antibody producing cells, secrete anti c-met IgG or TMX2 antibodies, depending on the antigen used. The aforementioned plasma cells can be rendered immortal by fusion with for example a HUNS1 cell line, and were found to also produce anti c-met IgG antibody after immortalization. In the case of an antibody against c-met, obtained antibody demonstrably decreased proliferation of cancer breast cell line MCF7.

It is therefore an object of the present invention to provide in general a process for the production of fully human, and more preferably monoclonal antibodies against a predefined antigen such as for example c-met and TMX-2, said process comprising the steps of:
  a) isolating peripheral blood mononuclear cells, preferably from blood;
  b) generating mononuclear cells from the isolated peripheral blood mononuclear cells;
  c) generating immature dendritic cells from the generated mononuclear cells;
  d) isolating CD4+ and CD19+ cells, preferably from blood;
  e) optionally pulsing at least the generated immature dendritic cells with the predefined antigen;
  f) co-culturing the immature dendritic cells, the CD4+ cells and CD19+ cells;
  g) pulsing at least the co-cultured immature dendritic cells, the CD4+ cells and CD19+ cells with at least the predefined antigen;
  h) generating mature dendritic cells from the immature dendritic cells by further co-culturing the immature dendritic cells, the CD4+ cells and CD19+ cells;
  i) inducing plasma cell formation;
  j) inducing or not inducing Ig class switching in the formed plasma cells.

It is further an object of the present invention to provide an antibody against a predefined antigen, obtained in general according to the process as described above, such as for example a human antibody against a predefined antigen such as for example c-met or TMX-2.

It is further an object of the present invention to provide a human antibody against human c-met, wherein said human antibody recognizes the amino acid sequence according to SEQ ID 1 and wherein it is preferably secreted by human plasma cells, more preferably by immortalized human plasma cells, as well as its use for the determining the presence or absence of human c-met in a sample or its use for treating cancer or a disease involving abnormal expression of c-met.

It is yet further an object of the present invention to provide a method for detecting the presence or absence of human c-met in a biological sample comprising the steps of
  a. contacting the sample with the above antibody, and
  b. detecting the presence or absence of an antibody-antigen complex formed by the antibody and the human c-met in said sample.

It is also an object of the present invention to provide a human antibody against human TMX2, wherein said human antibody recognizes the amino acid sequence according to SEQ ID 2 and wherein it is preferably secreted by human plasma cells, more preferably by immortalized human plasma cells, as well as its use for the determining the presence or absence of human TMX-2 in a sample or its use for treating cancer, in particular breast cancer or a disease involving abnormal expression of TMX2.

It is also an object of the present invention to provide a human antibody against human TMX2, wherein said human antibody recognizes the amino acid sequence according to SEQ ID 3 and wherein it is preferably secreted by human plasma cells, more preferably by immortalized human plasma cells, as well as its use for the determining the presence or absence of human TMX-2 in a sample or its use for treating cancer, in particular breast cancer or a disease involving abnormal expression of TMX2.

It is yet further an object of the present invention to provide a method for detecting the presence or absence of human TMX-2 in a biological sample comprising the steps of
  c. contacting the sample with the above antibody, and
  d. detecting the presence or absence of an antibody-antigen complex formed by the antibody and the human TMX-2 in said sample.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1. IgG detection using western blot in IL-4 treated (control), previous protocol and new improved protocol co-culture supernatants. IgG levels are increased in new protocol supernatants compared to both previous protocol and control cells. From right to left: Lane 1=Molecular weight marker (santacruz), Lane 2=control supernatant, Lane 3=previous protocol supernatant, Lane 4=improved protocol supernatant.

FIG. 5. c-met protein detection using our purified anti c-met IgG antibody. Commercially available antibody was also used, however c-met protein concentration was increased for better visualization of various bands detectable.

DESCRIPTION OF PREFERRED EMBODIMENTS

Figure 1:
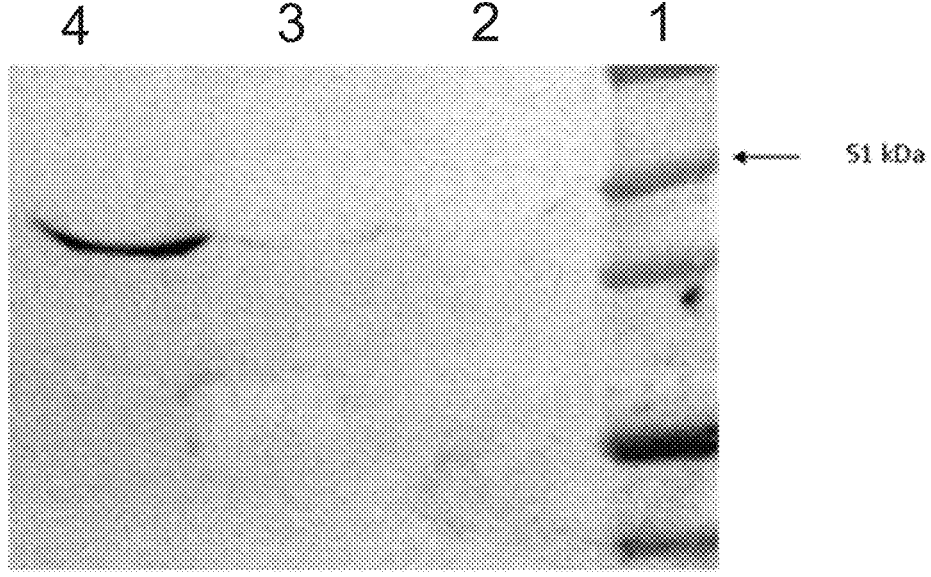
Figure 2A:
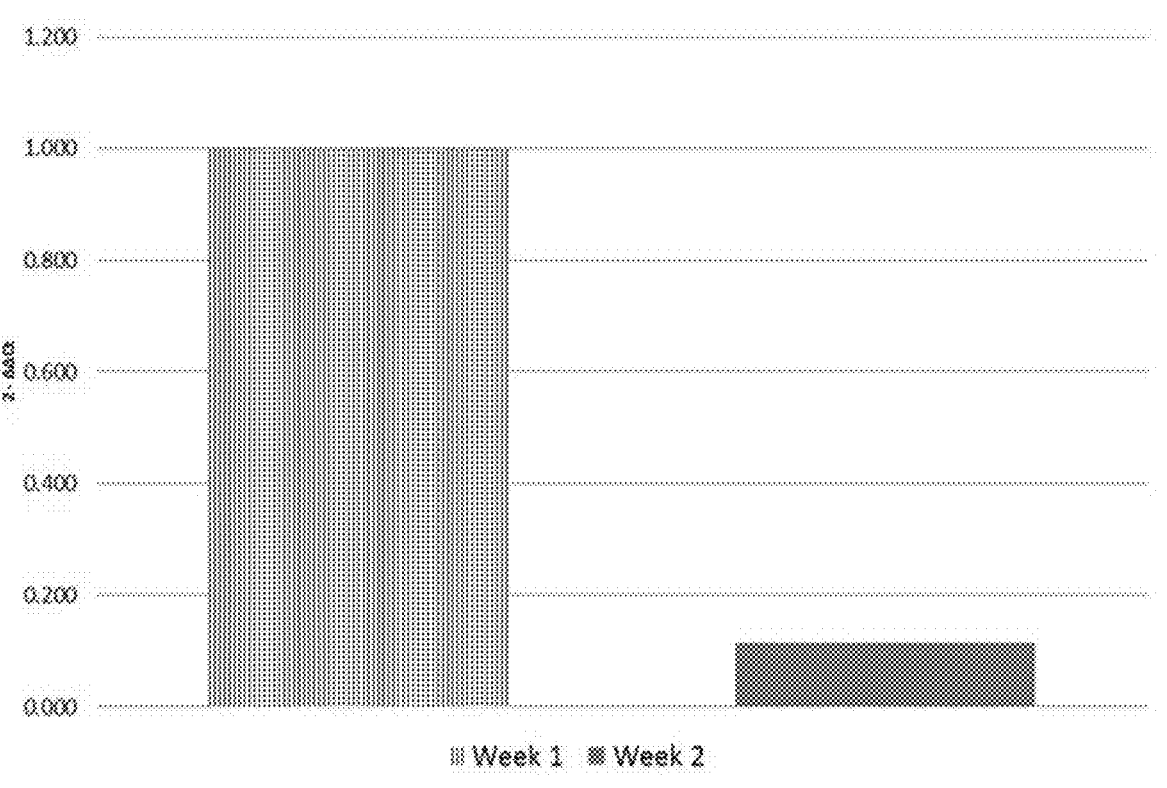
FIG. 2. qPCR results. a) Comparative qPCR data of IGHG gene expression in two different periods of time (end of week 1 and 2). Samples were normalized to week 1 sample with the Livak method and ACTB was used as the reference gene. b) Comparative qPCR data of various IG class expression at week 1 where optimum IGHG gene expression was found. Samples were normalized to IGHG gene expression with the Livak method and ACTB was used as the reference gene. IGHG is considered baseline 0 and hence bar is not apparent.
Figure 2B:
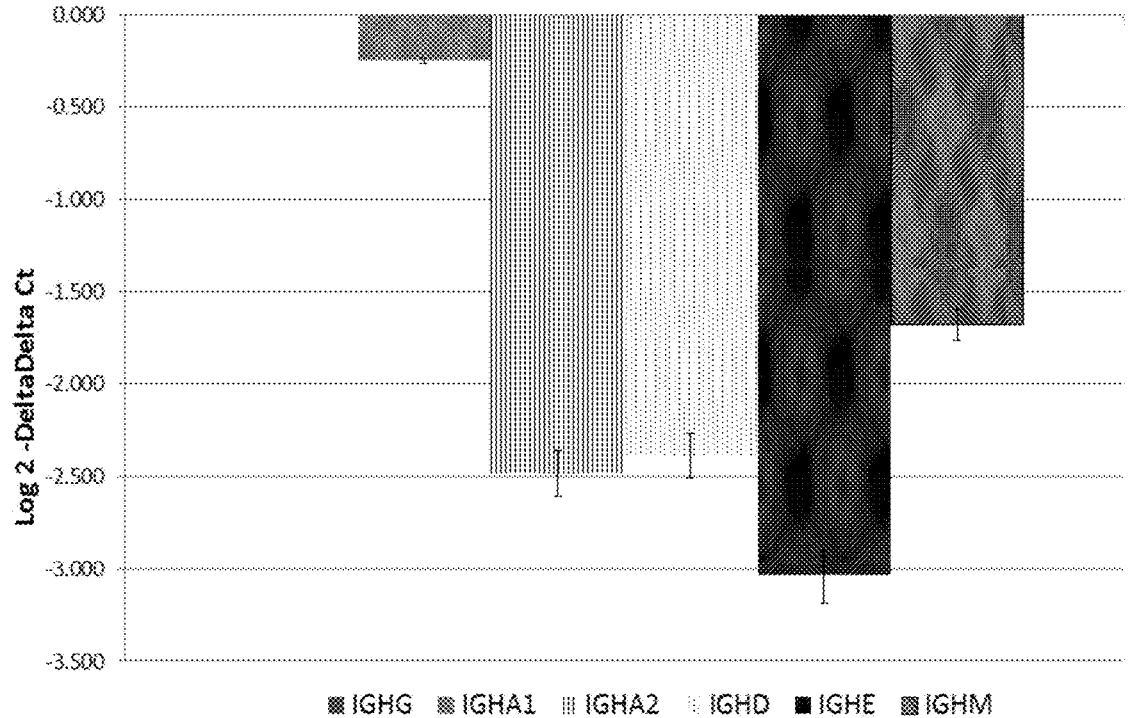
Figure 3:
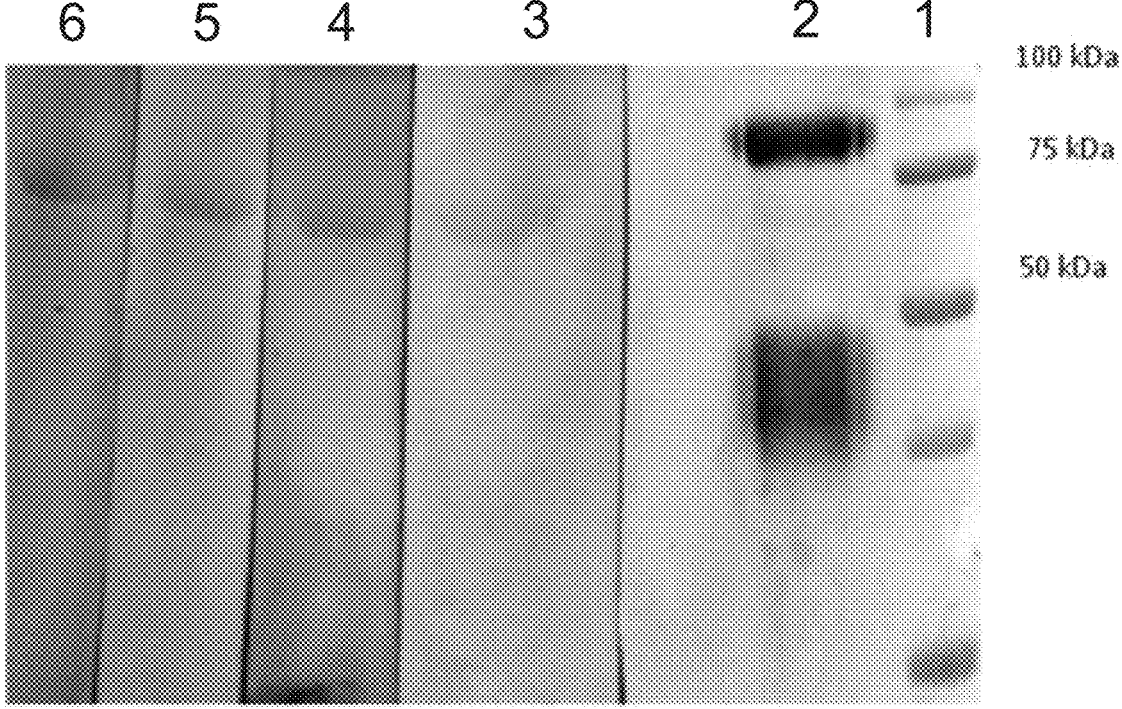
FIG. 3. c-met protein detection by western blot using co-culture supernatants from various experiments. Commercially available c-met polyclonal antibody was also used for comparison. c-met concentration was the same in all treatments. From right to left: Lane 1=molecular weight markers (BioRad), Lane 2 commercial polyclonal antibody, Lanes 3-6 co-culture supernatants from different experiments.
Figure 4:
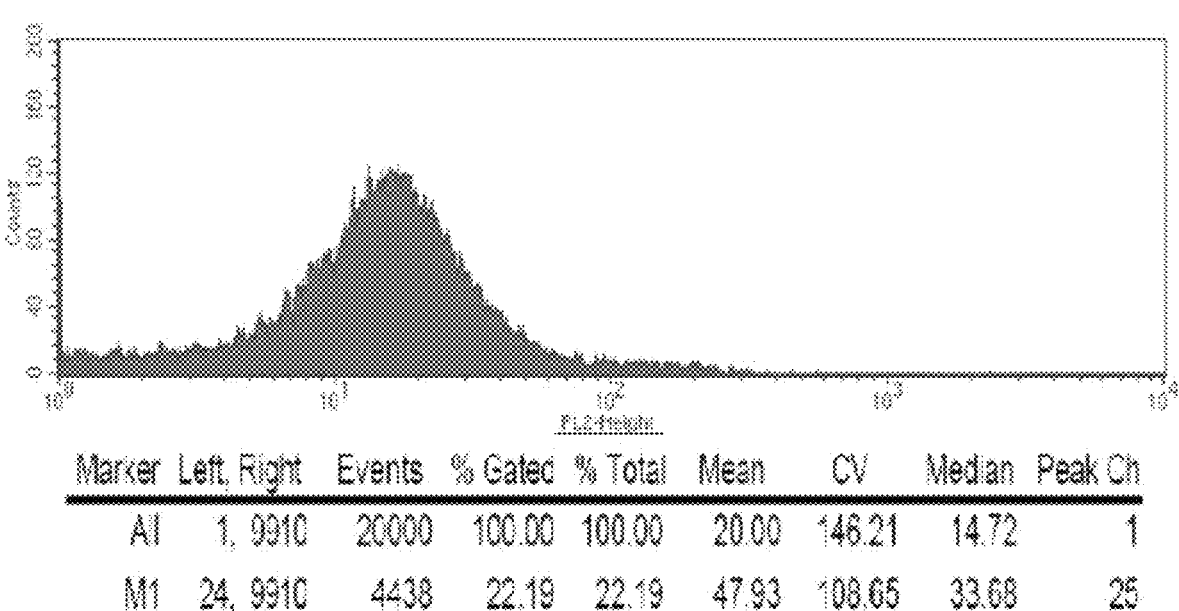
FIG. 4. MDA-MB-231 cells were used for the determination of c-met expression using both PE-commercial antibody and our FITCH-conjugated purified anti c-met IgG. Commercial antibody detects 22.19% positive events and our FITCH-purified antibody detects 19.02%. Samples contained equal cell numbers.
Figure 4:
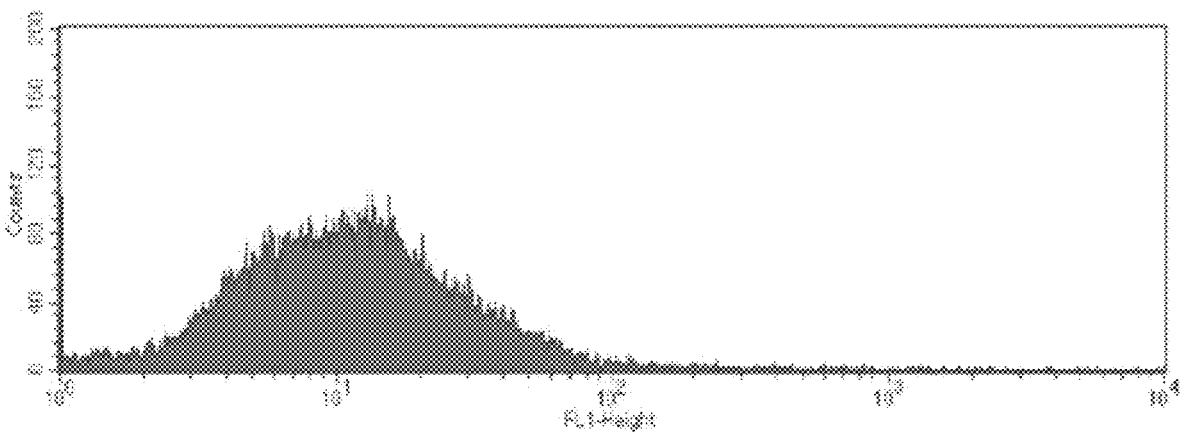
Figure 5A:
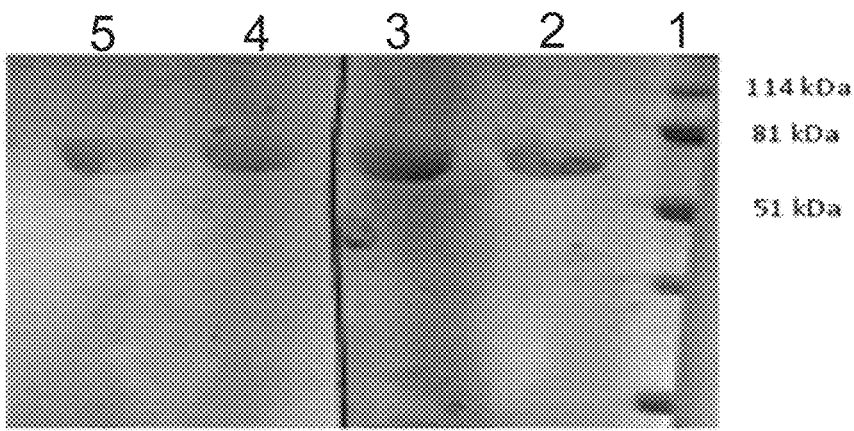
FIG. 5a from right to left, Lane 1: Molecular weight marker (santacruz), Lanes 2-5 various purified anti c-met IgG antibody preparations.
Figure 5B:
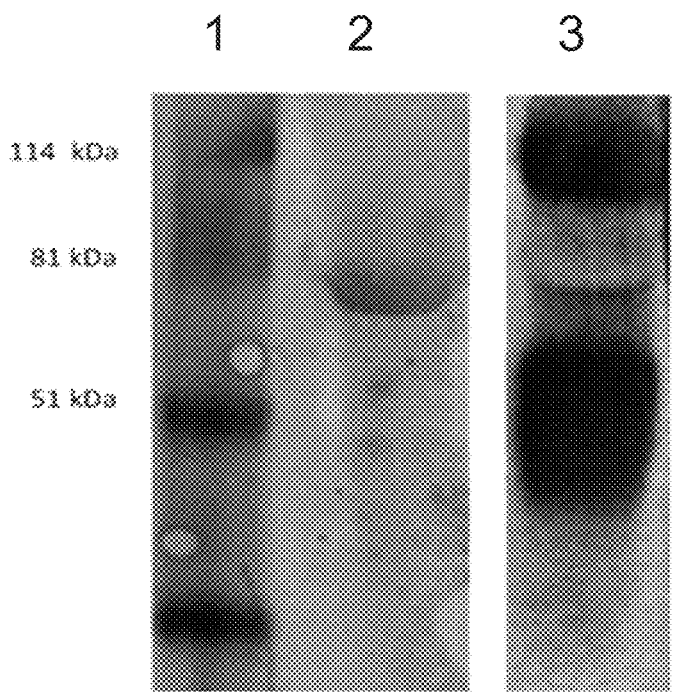
FIG. 5b from left to right, Lane 1: Molecular weight marker (santacruz), Lane 2: Purified c-met IgG antibody preparation, Lane 3: commercially available polyclonal antibody using c-met protein in excess in order to distinguish all the different bands recognised.
Figure 6:
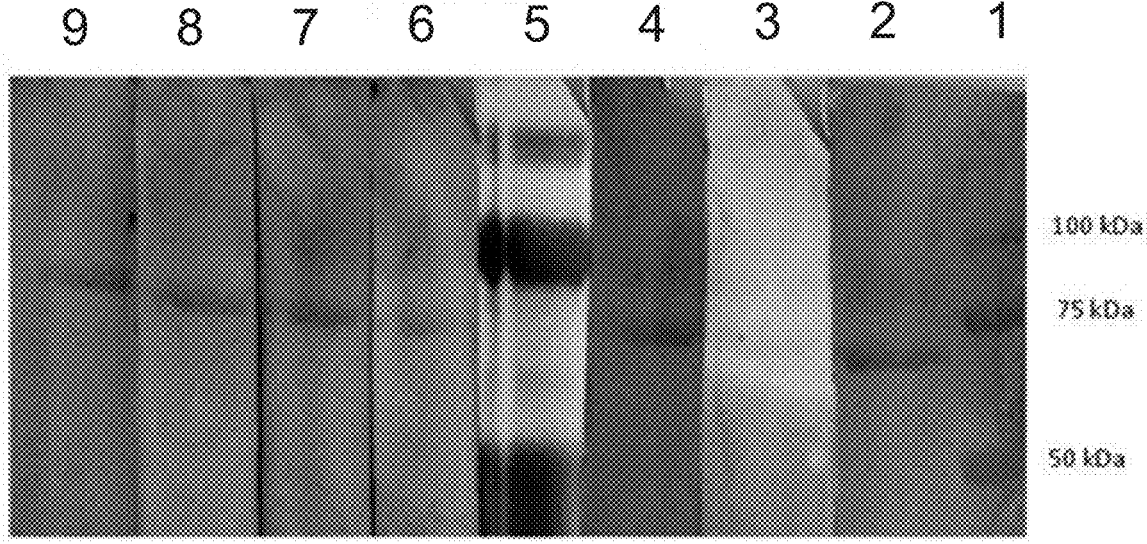
FIG. 6. c-met protein detection using fused CD138 supernatants. Our antibody can detect a single band of denatured c-met protein as opposed to commercially available polyclonal antibody. From right to left, Lane 1: molecular weight marker (BioRad), Lanes 2-4 various fused CD138 supernatants, Lane 5: commercially available antibody, Lanes 6-9 various fused CD138 supernatants.
Figure 7:
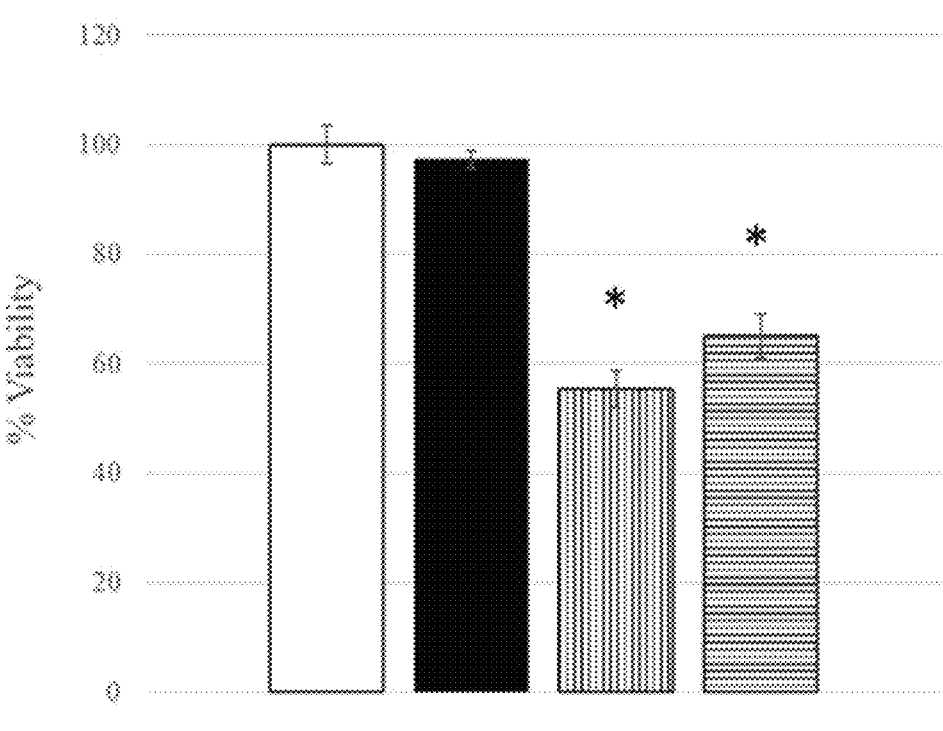
FIG. 7. The effect of CD138 supernatants containing c-met IgG on MCF-7 cell proliferation after 24 hr incubation. Cells were also treated with HGF in the presence or absence of supernatants. Results as expressed as % viable cells compared to control. Control vs. Fused supernatants p=0.000005, HGF vs HGF+Fused supernatants p=0.00015.

The process according to the present invention consists of the production of a true and fully human monoclonal antibody from human blood cells by mimicking the in vivo process.

The process according to the present invention provides in general a process for the production of preferably human, antibodies against a predefined antigen such as for example c-met and TMX-2, said process comprising the steps of:

a) isolating peripheral blood mononuclear cells, preferably from blood;

b) generating mononuclear cells from the isolated peripheral blood mononuclear cells;

c) generating immature dendritic cells from the generated mononuclear cells;

d) isolating CD4+ and CD19+ cells, preferably from blood;

e) optionally pulsing at least the generated immature dendritic cells with the predefined antigen;

f) co-culturing the immature dendritic cells, the CD4+ cells and CD19+ cells;

g) pulsing at least the co-cultured immature dendritic cells, the CD4+ cells and CD19+ cells with at least the predefined antigen;

h) generating mature dendritic cells from the immature dendritic cells by further co-culturing the immature dendritic cells, the CD4+ cells and CD19+ cells;

i) inducing plasma cell formation;

j) inducing or not inducing Ig class switching in the formed plasma cells.

In the initial step of the process according to the present invention, peripheral blood mononuclear cells from a bodily sample such as for example a bodily fluid, preferably from blood. In a preferred embodiment, the peripheral blood mononuclear cells (PBMCs) can be isolated using density gradient centrifugation, for example from freshly collected blood samples in vacutainers containing EDTA. Suitable separating solutions for use in density gradient centrifugation can be obtained from VWR under the trademark BIO-COLL. After density gradient centrifugation, the cell pellet comprising peripheral blood mononuclear cells can be re-suspended in a cell culturing medium such as for example RPMI medium supplemented with 10% FBS, 200 mM L-glutamine. Cell number and viability can be determined by Trypan Blue exclusion dye.

In the subsequent step b), the thus isolated peripheral blood mononuclear cells are incubated in a cell culturing medium in order to generate mononuclear cells from the isolated peripheral blood mononuclear. In a preferred embodiment, the peripheral blood mononuclear cells were incubated in a cell culturing medium in order to generate mononuclear cells at 37° C., 5% $CO_2$, in particular until adherence of mononuclear cells.

In a next step c), immature dendritic cells are generated from the previously generated mononuclear cells. After the incubation period yielding adherence of mononuclear cells, the supernatant is collected and adhered mononuclear cells were washed twice with warm phosphate-buffered saline (PBS). In a preferred embodiment, the mononuclear cells were incubated in the presence of granulocyte-macrophage colony-stimulating factor (GM-CSF) and interleukin 4 (IL-4), until immature dendritic cells are generated. In order to provide optimal conditions for the generation of the immature dendritic cells from the previously generated mononuclear cells, both granulocyte-macrophage colony-stimulating factor (GM-CSF) and interleukin 4 (IL-4), were replenished together with culturing medium every 2 days. The culture was kept until it was combined with a culture of CD4+ and CD19+ cells, as obtained in step d).

In a next step d), CD4+ and CD19+ cells were isolated from a bodily sample such as for example a bodily fluid, preferably from blood. In a preferred embodiment, the CD4+ cells can be isolated using anti-human CD4 magnetic beads. After centrifugation, the pellet of anti-human CD4 magnetic beads was re-suspended in RPMI culture medium containing 10% FBS and the supernatant is kept. Cell number and viability can be determined by Trypan Blue exclusion dye.

The supernatant that was kept and anti-human CD19 magnetic beads are added to isolate CD19+ by centrifugation. After centrifugation, the pellet of anti-human CD19 magnetic beads was re-suspended in complete medium. Cell number and viability can be determined by Trypan Blue exclusion dye.

The day of the co-culture, while iDC were pulsed with the peptide, CD4+ and CD19+ cells were isolated from freshly collected whole blood samples using the same method described before. Thus, the generated immature dendritic cells from step c) or e) were combined with the isolated CD4+ and CD19+ cells from step d) into a co-culture in step f).

In an optional next step e), which may be carried simultaneously to step d), the generated immature dendritic cells are pulsed with the predefined antigen. In a preferred embodiment, the immature dendritic cells are pulsed with the predefined peptide for to a period of approximately at least 4 hours, or from 4 hours to 10 hours or for 10 hours.

In the case where an antibody against c-met is to be obtained, the antigen is a 9-mer according to SEQ ID1, possessing the same immunogenicity as the whole c-met protein, is used. By choosing a short sequence of 9 residues as antigen, the possibility of polyclonal antibody generation is decreased. The antigen can be obtained by peptide synthesis techniques such as solid phase peptide synthesis. The antigen consists of 4 amino acids with a hydrophobic chain, 3 amino acids with a polar uncharged side chain, one amino acid with a positive charge and a glycine. The antigen according to SEQ ID1 has the sequence of H-VLPEFRDSY-OH.

In one case where an antibody against TMX2 is to be obtained, the antigen is a 9-mer according to SEQ ID2. The antigen is based on the TMX2 amino acid sequence at positions 86-95, which is modified by substitution of amino acid 87 (Glu) with Gln for enhanced immunogenicity. The antigen can be obtained by peptide synthesis techniques such as solid phase peptide synthesis. The antigen according to SEQ ID2 has the sequence of H-VQQHIGNIF-OH.

In another case where an antibody against TMX2 is to be obtained, the antigen is a 9-mer according to SEQ ID 3. The antigen is based on the TMX2 amino acid sequence at positions 173-181. The antigen can be obtained by peptide synthesis techniques such as solid phase peptide synthesis. The antigen according to SEQ ID 3 has the sequence of H-FAPIYADLS-OH.

After generating immature dendritic cells and optionally pulsing the immature dendritic cells with the predetermined antigen, and after isolating CD4+ and CD19+ cells, the immature dendritic cells, the CD4+ cells and CD19+ cells are combined and co-cultured in a step f). In a preferred embodiment, the ratio between immature dendritic cells to CD4+ cells and to CD19+ cell is such that the number of CD4+ cells and CD19+ cells are present in excess with respect to the number of immature dendritic cells and/or the number of CD4+ cells and CD19+ cells is approximately the same. As an example, a suitable number ratio between immature dendritic cells to CD4+ cells and to CD19+ cell is 1:10:10. In a preferred embodiment, the immature dendritic cells, the CD4+ cells and CD19+ cells are co-cultured in a suitable culturing medium, preferably RPMI culturing medium supplemented with 10% FBS, 200 mM L-glutamine and more preferably further comprising GM-CSF, IL-4, TNF-α, sCD40L, IL-6, IL-21, IL-10 and anti-human IgM. An exemplary RPMI culturing medium supplemented with 10% FBS, 200 mM L-glutamine can have 100 ng/ml GM-CSF, 50 ng/ml IL-4, 5 ng/ml TNF-α, 1 μg/ml sCD40L, 150 ng/ml IL-6, 50 ng/ml IL-21, 100 ng/ml IL-10, and 5 μg/ml IgM. A suitable culturing medium, such as for example RPMI culturing medium optionally supplemented with 10% FBS and 200 mM L-glutamine, may comprise a combination of GM-CSF, IL-4, TNF-α, sCD40L, IL-6, IL-21, IL-10 and anti-human IgM, in about 50-200 ng/ml GM-CSF, 2-100 ng/ml IL-4, 1-100 ng/ml nTNF-α, 0.5-50 ug/ml sCD40L, 50-500 ng/ml IL-6, 1-200 ng/ml IL-21, 30-300 ng/ml IL-10 and 1-50 ug/ml IgM. It is understood that where a given culturing medium is used in step f), the same culturing medium will be preferably used at least in the ensuing steps g) through j).

In a next step g), the immature dendritic cells, the CD4+ cells and CD19+ cells being co-cultured are pulsed with at least the predefined antigen. In a preferred embodiment, the antigen is added to the RPMI culturing medium optionally supplemented with 10% FBS and 200 mM L-glutamine, and more preferably further comprising GM-C SF, IL-4, TNF-α, sCD40L, IL-6, IL-21, IL-10 and anti-human IgM, preferably at a concentration of approximately 10 μg/ml The antigen is preferably added at a concentration of approximately 10 μg/ml within the first day of co-culturing the immature dendritic cells, the CD4+ cells and CD19+ cells.

In an next step h), mature dendritic cells were generated from the immature dendritic cells, preferably by co-culturing the immature dendritic cells, the CD4+ cells and CD19+ cells until mature dendritic cells are generated in the RPMI culturing medium optionally supplemented with 10% FBS and 200 mM L-glutamine, and more preferably further comprising GM-CSF, IL-4, TNF-α, sCD40L, IL-6, IL-21, IL-10 and anti-human IgM. During co-culturing, CD4+ and CD19+ cells are activated.

In the RPMI culturing medium optionally supplemented with 10% FBS and 200 mM L-glutamine, and more preferably further comprising GM-CSF, IL-4, TNF-α, sCD40L, IL-6, IL-21, IL-10 and anti-human IgM, GM-CSF is used for maturation of immature dendritic cells, antigen processing and antigen presentation, IL-4 is used for maturation of immature dendritic cells, inhibition of macrophage development, Th2 response and high MHCII expression, TNF-α was used as an inflammatory mediator for dendritic cells and T-cell activation, Th2 differentiation, MHCII up-regulation, sCD40L was used in dendritic cells for antigen presentation, MHCII upregulation, enhanced survival, for T-cell priming and CD4 expansion and for CD19 proliferation, IL-6, an inflammatory mediator was used for lymphocyte differentiation and cell survival/proliferation, IgM mimicked BCR binding to its cognate antigen and IL-10 and IL-21 were used for IgG class switching. There are several studies indicating the role of GM-CSF, IL-4 and TNF-α on DC maturation (see, e.g., Motta M R, Castellani S, Rizzi S, Curti A, Gubinelli F, Fogli M, Ferri E, Cellini C, Baccarani M, Lemoli R M (2003) Generation of dendritic cells from CD14+ monocytes positively selected by immunomagnetic adsorption for multiple myeloma patients enrolled in a clinical trial of anti-idiotype vaccination. British Journal of Haematology, 2003, 121, 240; and Zheng Z, Takahashi M, Narita M, Toba K, Liu A, Furukawa T, Koike T, Aizawa Y. (2000). Generation of dendritic cells from adherent cells of cord blood by culture with granulocyte-macrophage colony-stimulating factor, interleukin-4, and tumor necrosis factor-alpha. J Hematother Stem Cell Res; 9(4):453). However, a 2 stage maturation process involving GM-CSF and IL-4 also yielded immature dendritic cells.

The co-culture of immature dendritic cells, the CD4+ cells and CD19+ cells is carried out using antigen and factors mentioned below. In summary, GM-CSF was used for dendritic cells maturation, antigen processing and antigen presentation, IL-4 was used for DC maturation, inhibition of macrophage development, Th2 response and high MHCII expression, TNF-α was used as an inflammatory mediator for DC and T-cell activation, Th2 differentiation, MHCII up-regulation, sCD40L was used in DCs for antigen presentation, MHCII upregulation, enhanced survival, for T-cell priming and CD4 expansion and for CD19 proliferation, IL-6, an inflammatory mediator was used for lymphocyte differentiation and cell survival/proliferation, IgM mimicked BCR binding to its cognate antigen and IL-10 and IL-21 were used for IgG class switching.

In a next step i), plasma cell formation is induced, and in particular the CD19+ cells in the co-culture of immature dendritic cells, the CD4+ cells and CD19+ cells form plasma cells. Depending on the antigen used in the process according to the present invention, plasma cells will secrete pure and fully human monoclonal antibodies against the predetermined antigen.

In a next step j), Ig class switching can be induced, and can be induced in particular in the formed plasma cells. Ig class switching allows excising unwanted Ig genes in the plasma cells so that only the desired gene can be expressed. B-cells such as CD19+ cells express IgM/IgD in their surface, but once activated can express IgA, IgE, IgG or retain their IgM expression depending on the stimuli received by T-cells. Thus in a preferred embodiment of the present invention, it can be advantageous to induce Ig class switching towards IgG expression in the plasma cells. In the RPMI culturing medium optionally supplemented with 10% FBS and 200 mM L-glutamine, and more preferably further comprising GM-CSF, IL-4, TNF-α, sCD40L, IL-6, IL-21, IL-10 and anti-human IgM, IL-10 and IL-21 were added to the co-culture to facilitate IgG class switching.

In a further step k), the plasma cells producing the antibody can be immortalized by fusion with a cancer cell line. In order to immortalize the plasma cells, the plasma cells generated from the co-culture can be isolated by flow cytometry using CD138-PE and then be fused to HUNS1 cells. As an example, CD138 positive plasma cells can be added with approximately 10 times the number of HUNS1 cells and the fusion can be carried out using 50% PEG solution, following the protocol of the manufacturer Sigma. Finally, fused cells were let to growth in RPMI, 10% FBS, 200 mM L-glutamine until loss of IgG secretion.

In a preferred embodiment, the cells that are isolated are autologous cells, which is advantageous in particular when the antibodies are used in a therapeutical context, as the antibodies can then also be considered to be autologous.

The antibodies of the present invention may then be isolated after step j) or k) using well-known techniques in the art such as for example, but not limited to, physico-chemical fractionation or affinity purification.

The antibodies of the present invention can be used to detect the presence of malignant tumors for which abnormal c-met and TMX2 expression is observed in biological samples such as for example in blood samples. The antibodies can be used to detect human c-met and human TMX2 found in biological samples such as blood samples of a patient which is suspected of being impeded by or afflicted with a proliferative disease such as cancer and thus to rapidly and readily determine if the impediment or disease is linked to abnormal c-met and TMX2 expression. Reagents and techniques for qualitatively and quantitatively determining the presence or absence of a particular antigen using an antibody are well known in the art. Examples are for example ELISA and Western blotting.

The antibodies of the present invention can thus be used to diagnose cancer using the antibodies of the present invention. The antibodies of the present invention can be used in cancer diagnostics or in diagnosing of any disease involving abnormal expression of c-met and/or TMX2 because they specifically bind to markers of cancer as set forth above. It has been further been found that the monoclonal antibodies of the present invention limit the proliferation of cancer cells exhibiting over-expression of c-met and/or TMX2. Expression levels of c-met and/TMX-2 may be determined via qPCR using specific primers for c-met and/or TMX2, where relative quantification was performed according to Livak method using a housekeeping gene such as for example 18SrRNA. In the context of the present invention, abnormal expression is used interchangeably with over-expression.

The antibodies of the present invention can be used as biomarkers in diagnose of cancer, especially in malignant or benign breast cancer or in the monitoring of disease progression.

In a further embodiment of the present invention, the antibodies of the present invention can also to form antibody conjugates which can be conjugated to particles, small molecules or drugs. The antibody conjugates can be used in tumor imaging and detection and/or targeted drug delivery and/or other therapeutic interventions such as thermo-therapy.

The antibodies of the present invention can be used as active ingredient in pharmaceutical compositions for preventing and/or treating malignant tumors where c-met and/or TMX2 expression plays a role in cancer formation and/or progression.

The antibodies of the present invention can also be used for preventing and/or treating diseases involving c-met and/or TMX2 proteins.

The antibodies of the present invention can be used to prevent and/or treat cancers by decreasing cell proliferation caused by abnormalities and the metastasis of cancer cells where c-met and TMX2 expression abnormalities are involved.

The antibodies of the present invention can be used to prevent and/or treat diseases involving c-met and TMX2 proteins by decreasing cell proliferation caused by c-met and TMX2 expression abnormalities.

The present invention provides antibodies against human c-met and TMX2. Using the antibodies of the present invention it is possible to readily and reliably detect the presence or absence of c-met and TMX2. The present invention is thus useful in the field of medical diagnosis and treatment. Further, the antibodies of the present invention can be also used in the field of pharmaceuticals such as cancer diagnosis and treatment because they affect the functions of cancer cells relating to c-met and TMX2.

EXPERIMENTAL DATA

Determining IgG
IgG Secretion by ELISA

Secreted IgG was determined by a human IgG Elisa Quantitation Set (Bethyl) according to the manufacturer's instructions. Briefly, a standard curve using known concentrations of human serum IgG was constructed. 100 ul of each supernatant was used and IgG concentration was calculated based on the standard curve obtained. Antibodies used react specifically with Human IgG, not with other human immunoglobulins or other human serum proteins. Absorbance was read at 450 nm using a uQuant Elisa microplate spectrophotometer. The same protocol was used for TMX2 antibody as well. IgG concentration in ng/ml was determined using Elisa immunoassay based on human IgG of known concentrations. Mean IgG concentration in co-culture supernatants was found to be 4 ng/ml. For TMX2 IgG concentration was 50 ng/ml.

IgG Secretion by Western Blot

Next, IgG secretion was determined in supernatants using standard Western Blot. After electrophoresis samples were transferred onto nitrocellulose membrane. Membranes were blocked with 5% BSA in TBS/Tween 20 for 1 hr and then probed with a goat anti human IgG antibody. After washing with TBS/Tween 20, membranes were incubated with the appropriate anti-human IgG-AP secondary antibody. Membranes were washed again with PBS/Tween and signal was detected using BCIP/NBT solution until color development. Results were detected and analyzed using Image Lab software. Detectable levels of IgG were found in co-culture supernatants denoting antibody secretion.

IgG RNA Expression—PCR

Total RNA from cells was extracted using RNeasy Mini Kit and DNA elimination was performed using DNase. Samples were evaluated spectrophotometrically. Then, 1 μg of each RNA sample was used as a template for cDNA synthesis using a PrimeScript RT Reagent Kit. Real-time qPCR was then performed using KAPA SYBR Fast Master Mix (2×) Universal. Specific primers for each marker and the reference gene (ACTB) were designed using Gene Expression 1.1 software. Primer sequences were evaluated by BLAST searching to exclude those that would amplify undesired genes (Table 1). PCR program was as follows: initial denaturation at 95° C. for 3 min, 40 cycles of denaturation at 95° C. for 5 s followed by annealing at 59° C. for 10 s. Melting curve analysis was performed from 70° C. to 90° C. with 0.5° C. increments for 5 s at each step. qPCR products were run on agarose gels to validate the results. Regarding IGHG gene expression, it was higher during the first week of co-culture, while it decreased up to 85% during the second week.

Determining Anti C-met Activity

By ELISA

Sample anti c-met activity was determined by ELISA in comparison with a commercially available antibody. Briefly, 96 well plates were incubated with c-met protein in carbonate/bicarbonate buffer and incubated overnight at 4° C. Wells were washed with washing buffer and blocked with blocking buffer. Then 100 ul supernatant or c-met commercial antibody were added to each well and incubated overnight at 4° C. Wells were washed with washing buffer and HRP conjugated Goat Anti-Human IgG antibody or HRP conjugated Goat anti-mouse IgG antibody were added. Wells were then washed with washing buffer. 100 ul TMB substrate solution were added in each well and incubated for 30 mins in the dark. The reaction was stopped by the addition of 100 ul stop solution and absorbance was determined at 450 nm using a uQuant microplate spectrophotometer. The same protocol was used for TMX2 antibody as well. Absorbance using co-culture antibody against c-met protein was determined compared to the absorbance of a commercial antibody against the same concentration of c-met. Results were calculated using the absorbance of commercial antibody as the optimal 100% binding efficiency. Mean binding efficiency of co-culture Ab was 12.7%. For TMX2 binding efficiency was 20%.

By Western Blot 5 ug recombinant human c-met protein were denatured and electrophoresed as previously. Transfer was performed at 10V, 1 hr and after blocking for 1 hr, membranes were incubated by either culture supernatants in blocking buffer (1:50) or a commercially available human HGFR/c-met goat polyclonal Ab. Incubation was carried out at 4° C., overnight. Appropriate AP-secondary antibodies were used and results were analyzed using Image Lab software. Commercial polyclonal antibody recognizes numerous sites whereas the antibody of the present invention produces a signal band.

Production of Anti C-met IgG

Figure 8:
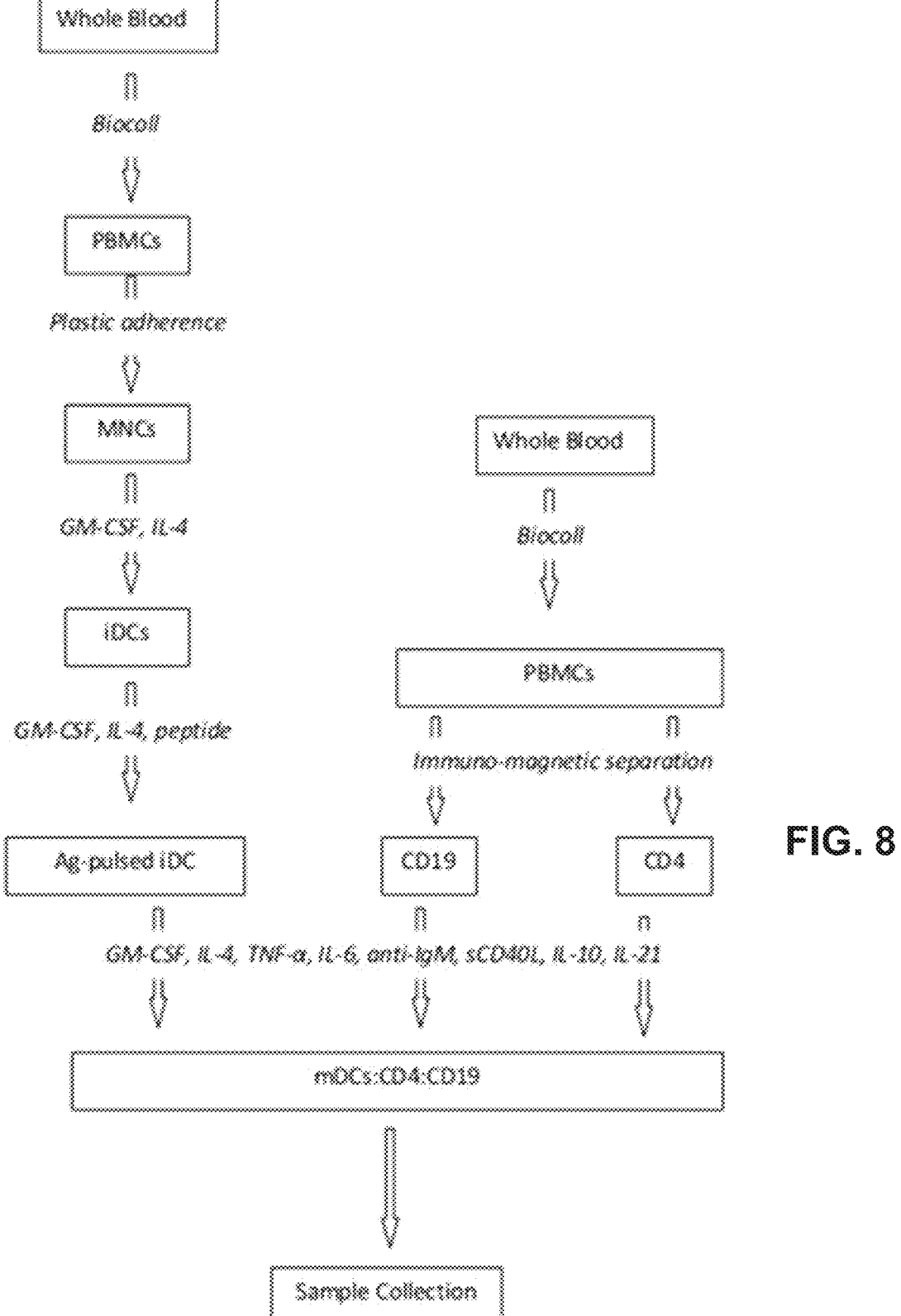
FIG. 8 shows a flow diagram of the process according to one embodiment the present invention.
Figure 9:
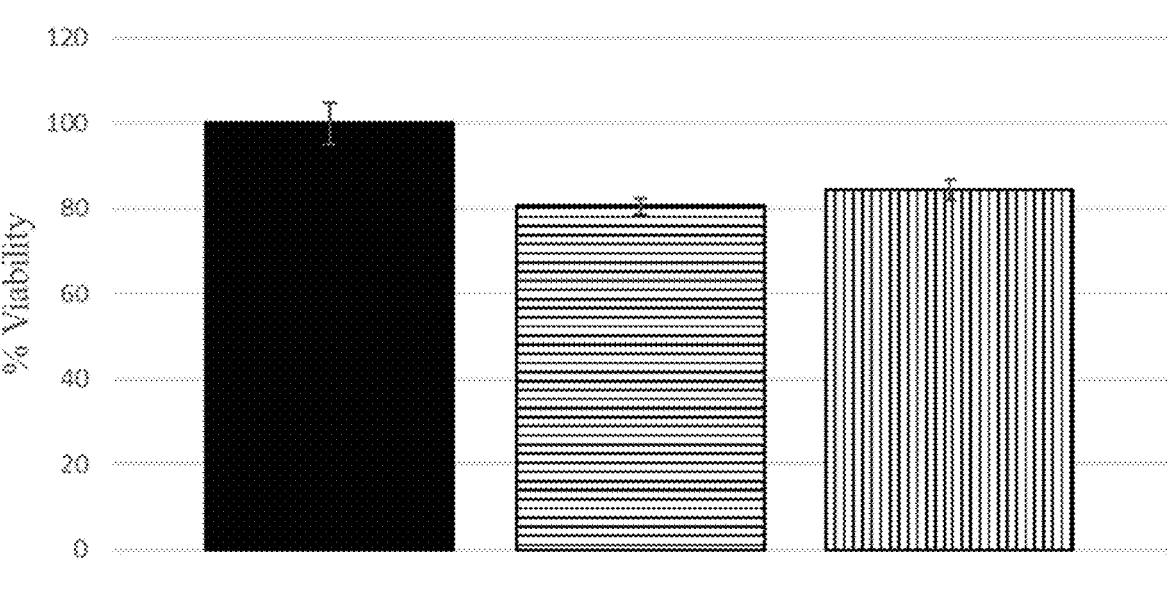
FIG. 9 shows the effect of co-culture supernatants containing TMX2 IgG on MCF-7 cell proliferation after 24 hr incubation. Results as expressed as % viable cells compared to control. Control vs. TMX2 Ab from 1st Experiment p=0.004, Control vs. TMX2 Ab from 1st Experiment p=0.018.
Figure 10:
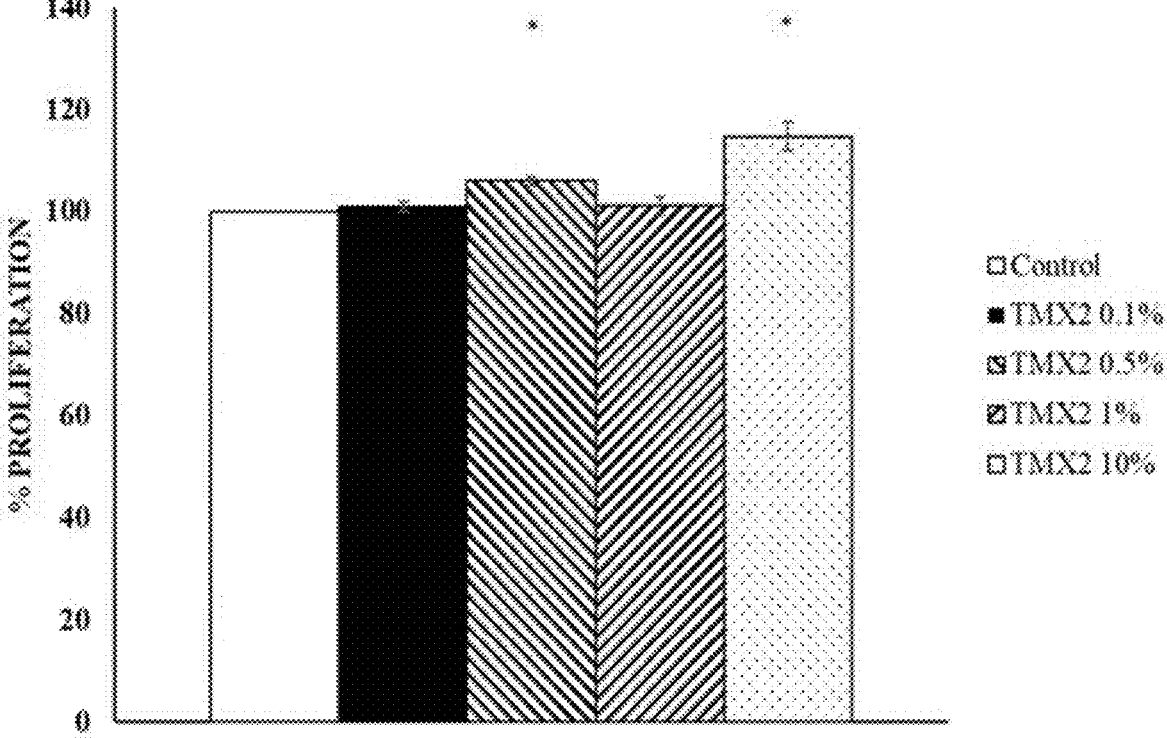
FIG. 10 The effect of TMX2 SEQ ID 2 on MCF-7 cell proliferation. Bars represent means±SEM. Control vs TMX 0.1%: 100 vs 100.9, p-value=NS; Control vs TMX 0.5%: 100 vs 1005.9, p-value=0.0007; Control vs TMX 1%: 100 vs 101.1, p-value=NS; Control vs TMX 10%: 100 vs 114.7, p-value=0.0001.
Figure 11:
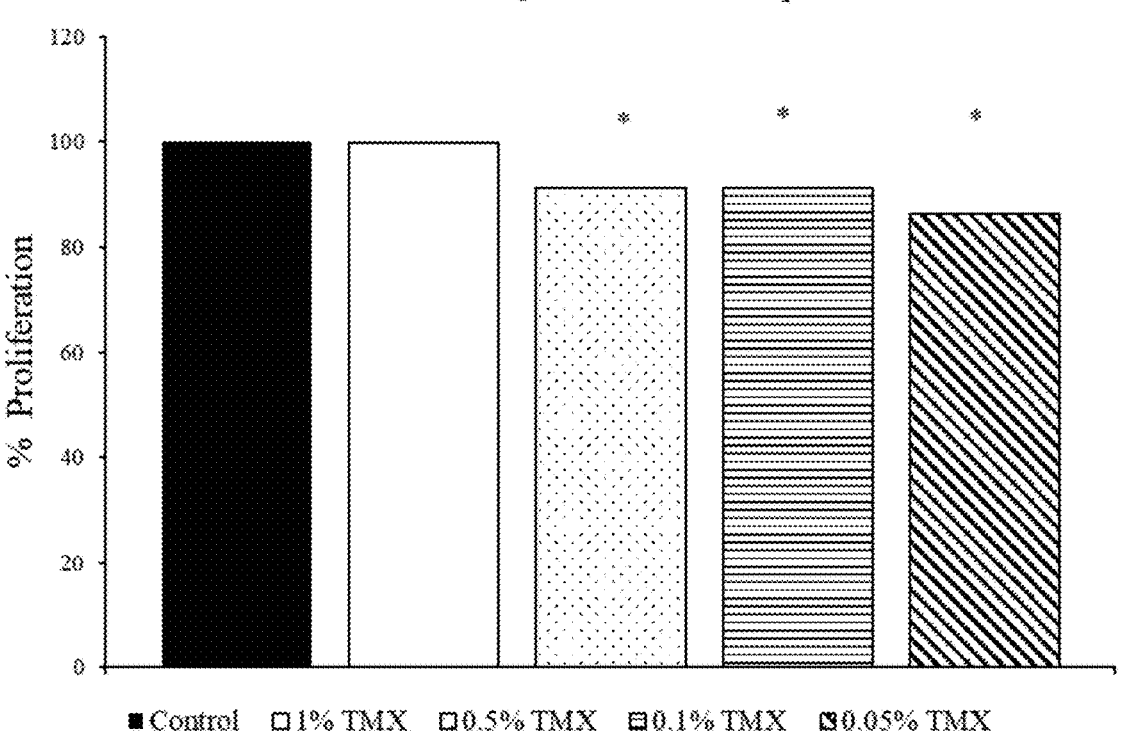
FIG. 11 The effect TMX2 IgG SEQ ID 3 on MCF-7 cell proliferation. Results are expressed as % viable cells compared to control. Control vs. 0.5 TMX p=0.03; Control vs. 0.1% TMX p=0.0006; Control vs. 0.05% TMX p=0.01.

For plasma cell generation capable of antibody production, first immature dendritic cells were generated from mononuclear cells and pulsed with the peptide of choice. Then, immature dendritic cells were fully matured in the presence of CD4 and CD19 cells. CD4 cells were activated and CD19 cells were transformed into antibody producing plasma cells. During the whole procedure, cells were incubated in the presence of growth factors mimicking inflammatory environment and promoting IgG class switch. A schematic representation of the procedure according to the present invention can be seen in FIG. 8.

In order to isolate c-met IgG antibody from culture supernatants, affinity chromatography was used. First collected samples were passed through an EpiMAX Affinity Purification Kit where the column was loaded with the specific 9-mer peptide used in cell culture. Purification was performed as per manufacturer's instructions. C-met positive eluent was immediately passed through a MAb Trap Kit as per manufacturer's protocol for IgG isolation. The eluent obtained contained anti-c met IgG Ab.

By Flow Cytometry 2 ml from the eluted IgG/c-met positive sample was speed vac for 4 hr, no heat, low drying rate until concentrated to 200 ul. Protein content determined by microBCA was 12 ug/ml. 100 ul were used for c-met protein detection by western blot and 200 ul were used for flow cytometry. Briefly, 200 ul of the concentrated sample was conjugated with FITC using Abcam's FITC Conjugation Kit according to the manufacturer's instructions. Conjugated Ab was then used for flow cytometry analysis.

For Flow cytometry, $10^5$ MDA-MB-231 cells for each treatment were used. Cells were centrifuged at 500 g for 10 mins and either 5 ul anti-hHGFR/c-MET-PE commercial antibody or 200 ul supernatant-FITC was added to the pellet. Unstained cells served as the control. After 30 mins incubation in the dark, 3 ml 0.5% FBS in PBS was added to each vial and centrifuged for 5 mins, 500 g. Supernatant was discarded and pellet was re-suspended in 0.5 ml PBS. Commercial Ab detected 22.19% events, whereas the antibody of the present invention detects 19%.

By Western Blot

Purified supernatants from chromatography columns were used as primary antibody for a western blot experiment. 5 ug c-met protein was run in a 10% polyacrylamide gel. Whole procedure was performed as already stated. Supernatants were diluted 1:50 in blocking buffer. Results were analyzed using Image Lab software. The antibody of the present invention still detects only one c-met band demonstrating its high specificity.

Fusion

Supernatants from fused CD138 positive cells and HUNS1 were collected weekly and tested as well using Elisa and western blot for c-met detection.

By Elisa 100 ul of fused supernatants were tested for c-met activity using Elisa as already stated. Mean binding efficiency of fused Ab was 9.3±3.8% ng/ml. IgG determination in fused cells was not possible due to the fact that HUNS1 secreted IgG as well.

By Western Blot

Supernatants from fused cultures were used as primary antibody is a western Blot experiment as already described. Again the antibody of the present invention detected one band for c-met.

Biological Activity of Antibodies

MCF-7 cell line was used to test antibody efficiency. The effect of produced antibody on cell proliferation was tested by MTT assay. Briefly, 10,000 cells/well were added to each well in a 96 well tissue culture plate and left overnight for adherence. Cells were treated for 24 hr with HGF 100 ng/ml in the presence or absence of fused CD138 supernatants collected during consecutive weeks. After the incubation period, 20 ul (5 mg/ml) MTT reagent was added and left for As far as TMX2 is concerned, cells were treated with co-culture supernatants containing secreted TMX2 IgG (1:4 dilution with medium, 200 ul total volume/well) for 24 hr. TMX2 antibodies were taken from 2 separate experiments (TMX2 Ab_Exp1, TMX2 Ab_Exp2). After the incubation period, 20 ul (5 mg/ml) MTT reagent was added and left for 3 hr inside the incubator until formazan crystal formation. Crystals were dissolved by the addition of 100 ul DMSO and absorbance was read at 570 nm using a uQuant Elisa Reader. Cell viability was expressed as a percentage of viable cells in the treated groups compared to the untreated control group. Supernatants from both experiments decreased cell proliferation significantly (Control vs TMX2 Ab_Exp1, $100\pm5\%$ vs $80.5\pm1.8\%$, p=0.004; Control vs TMX2 Ab_Exp2, $100\pm5\%$ vs $84.3\pm2.4\%$, p=0.018).

```
                           SEQUENCE LISTING

<160> NUMBER OF SEQ ID NOS: 3

<210> SEQ ID NO 1
<211> LENGTH: 9
<212> TYPE: PRT
<213> ORGANISM: Homo sapiens

<400> SEQUENCE: 1

Val Leu Pro Glu Phe Arg Asp Ser Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic sequence, designed peptide based on
      TMX2 AA sequence 86-95 modified by substitution of AA87 (Glu) with
      Gln

<400> SEQUENCE: 2

Val Gln Gln His Ile Gly Asn Ile Phe
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic sequence, designed peptide based on
      TMX2 AA sequence 173-181

<400> SEQUENCE: 3

Phe Ala Pro Ile Tyr Ala Asp Leu Ser
1               5
```

3 hr inside the incubator until formazan crystal formation. Crystals were dissolved by the addition of 100 ul DMSO and absorbance was read at 570 nm using a uQuant Elisa Reader. Cell viability was expressed as a percentage of viable cells in the treated groups compared to the untreated control group. Supernatants alone caused a significant decrease in MCF-7 proliferation (control vs Fused supernatants, $100\pm3.4\%$ vs $55.3\pm3.3\%$, p=0.000005). HGF addition did not affect cell proliferation possibly due to high cell density, however addition of fused supernatants in the presence of HGF caused a significant decrease in cell proliferation (HGF vs HGF+Fused supernatants, $97.3\pm1.5\%$ vs $65.1\pm3.9\%$, p=0.00015).

The invention claimed is:

1. A process for the production of monoclonal human antibodies by human cells, against a predefined antigen, said process comprising the steps of:
   a) isolating peripheral blood mononuclear cells from blood;
   b) generating mononuclear cells from the isolated peripheral blood mononuclear cells;
   c) generating immature dendritic cells from the generated mononuclear cells;
   d) isolating CD4+ and CD19+ cells from blood;
   e) pulsing at least the generated immature dendritic cells with the predefined antigen, without CD4+/CD19+ cells present;

f) co-culturing the immature dendritic cells, the CD4+ cells and CD19+ cells in a culturing medium comprising a combination of GM-CSF, IL-4, TNF-α, sCD40L, IL-6, IL-21, IL-10 and anti-human IgM;

g) pulsing at least the co-cultured immature dendritic cells, the CD4+ cells and CD19+ cells with at least the predefined antigen;

h) generating mature dendritic cells from the immature dendritic cells by further co-culturing the immature dendritic cells, the CD4+ cells and CD19+ cells;

i) inducing plasma cell formation; and j) inducing or not inducing Ig class switching towards IgG expression in the formed plasma cells.

2. The process according to claim 1, wherein the formed plasma cells are subsequently immortalized by fusion with a cancer cell line.

* * * * *